United States Patent [19]

Eistetter et al.

[11] 4,198,424

[45] Apr. 15, 1980

[54] SUBSTITUTED 1-PHENYL-2-PYRROLIDIN-2-YL-ETHANOLS, THEIR SYNTHESIS, THEIR USE AND THEIR COMPOSITIONS

[75] Inventors: Klaus Eistetter, Constance; Hans-Peter Kley, Allensbach, both of Fed. Rep. of Germany

[73] Assignee: Byk Gulden Lomberg Chemische Fabrik GmbH, Constance, Fed. Rep. of Germany

[21] Appl. No.: 965,147

[22] Filed: Nov. 30, 1978

[30] Foreign Application Priority Data

Dec. 1, 1977 [LU] Luxembourg ............................ 78625

[51] Int. Cl.$^2$ .................. C07D 405/10; C07D 207/44; A61K 31/40
[52] U.S. Cl. ................................ 424/274; 260/326.47; 260/326.5 R; 260/326.5 D; 260/326.5 M
[58] Field of Search ................ 260/326.5 M, 326.5 R, 260/326.5 D, 326.36, 326.47; 424/274

[56] References Cited

U.S. PATENT DOCUMENTS

| | | | |
|---|---|---|---|
| 3,591,602 | 7/1971 | Lockhart | 260/326.5 M |
| 3,637,742 | 1/1972 | Lockhart | 260/326.5 M |
| 3,652,587 | 3/1972 | Lockhart | 260/326.5 M |
| 3,745,171 | 7/1973 | Lockhart | 260/326.5 M |
| 4,077,982 | 3/1978 | Young et al. | 260/340.7 |
| 4,094,987 | 6/1978 | Hasspacher et al. | 260/326.5 M |
| 4,123,545 | 10/1978 | Hasspacher et al. | 260/326.5 M |

*Primary Examiner*—Jose Tovar
*Attorney, Agent, or Firm*—Berman, Aisenberg & Platt

[57] ABSTRACT

Selected substituted 1-phenyl-2-pyrrolidin-2-yl-ethanols and their pharmacologically-acceptable acid-addition salts are useful as analgesics in human and veterinary medicine. Such compounds are prepared by reducing corresponding substituted 1-phenyl-2-pyrrolidin-2-yl ethanones and are formulated into medicinal compositions suitable for administration.

22 Claims, No Drawings

SUBSTITUTED 1-PHENYL-2-PYRROLIDIN-2-YL-ETHANOLS, THEIR SYNTHESIS, THEIR USE AND THEIR COMPOSITIONS

BACKGROUND 2-phenacylpyrrolidines are described by R. B. Herbert et al. (*J.C.S., Chem. Comm.*, 1976, 450–451) as intermediates for alkaloids of the septicin type. From U.S. Pat. Nos. 3,931,155 and 3,882,104 1-(aryl-substituted-phenyl)-2-pyrrolidin-2-yl-ethanones and -ethanols (intended to be used as anticoagulants) are known. The properties of certain pyrrolidin-2-yl-ethanones and -ethanols as inhibitors of blood platelet aggregation were investigated by J. M. Grisar et al. [*J. Med. Chem.*, 19 (1976) 1195 to 1201].

SUMMARY OF THE INVENTION

Various aspects of the subject invention are inseparable from compounds which, in free-base form, are of the formula

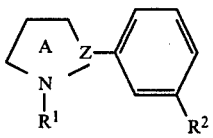

wherein
  A is a 5-membered ring;
  Z is
    (1) $>\overset{*}{C}H—CH_2—CO—$,
    (2) $>C=CH—CO—$ or
    (3) $>\overset{*}{C}H—CH_2—\overset{*}{C}H(OR^7)—$;
  $R^1$ is $—C_{n-1}H_{2n-1}$;
  $R^2$ is chloro, hydroxy (—OH), alkyl with from 1 to 4 carbon atoms or alkoxy with from 1 to 4 carbon atoms;
  $R^7$ is hydrogen, acyl, alkyl with from 1 to 7 carbon atoms or tetrahydropyranyl;
  n is a positive whole number of at most 8 and
  * designates an asymmetric carbon atom.

Reference is made to "free-base form" to include both the free base and its acid-addition salts. Reduction of those compounds wherein Z is (1) or (2) yields their counterparts wherein Z is (3) and $R^7$ is hydrogen. These are converted in compounds wherein $R^7$ is acyl or alkyl or tetrahydropyranyl, respectively, by esterification or etherification, respectively. As the free bases [wherein Z is (3)] have useful analgesic activity, they and their pharmacologically-acceptable acid-addition salts are advantageously used in human and veterinary medicine to alleviate pain; as toxic acid-addition salts are readily converted to corresponding free bases or to pharmacologically-acceptable acid-addition salts, they are also useful.

Pharmacologically-acceptable compounds wherein Z is (3) are conventionally compounded into medicinal compositions, including virtually all standard dosage forms for normal modes of administration.

DETAILS 1-phenyl-2-pyrrolidin-2-yl-ethanols (substituted in the 3-position of the phenyl ring by specific substituents as well as their esters and ethers have unexpected and advantageous properties, particularly those substituted 1-phenyl-2-pyrrolidin-2-yl ethanols (a) of the formula

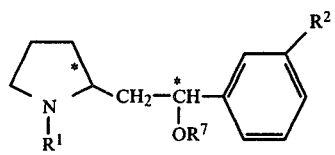

wherein
  $R^1$ denotes a hydrogen atom (—H) or alkyl with from 1 to 7 carbon atoms,
  $R^2$ denotes chloro, hydroxyl (—OH), alkyl with from 1 to 4 carbon atoms or alkoxy with from 1 to 4 carbon atoms, and
  $R^7$ denotes a hydrogen atom, acyl, alkyl with from 1 to 7 carbon atoms or tetrahydropyranyl,
and their acid-addition salts.

Suitable alkyl groups are straight-chain or branched alkyl radicals. Straight-chain alkyl radicals with from 1 to 7 carbon atoms are, for example, methyl, ethyl, n-butyl and n-heptyl, of which those with from 1 to 3 carbon atoms (particularly methyl) are preferred. Branched alkyl radicals with from 3 to 7 carbon atoms include, inter alia, isopropyl, sec.-butyl, tert.-butyl, tert.-pentyl and 2-methylpentyl, of which those with 3 or 4 carbon atoms are preferred. As alkyl radicals of alkoxy group, both straight-chain and branched alkyl radicals are suitable.

As acyl groups those are suitable which are derived from carboxylic acids usually employed in galenic chemistry. There are mentioned for example alkanoyl groups with from 1 to 11, preferably 2 to 7 carbon atoms, such as the heptanoyl, caproyl, pivaloyl, butyryl, isobutyryl or propionyl group, particularly the acetyl group.

As salts, all acid-addition salts are suitable. Particularly important are the pharmacologically-compatible salts of inorganic and organic acids usually employed in galenic medicine. Pharmacologically-incompatible salts are readily converted into pharmacologically-compatible salts by processes known to one skilled in the art. Illustrative salts include, for example, water-soluble or water-insoluble acid-addition salts, such as the hydrochloride, hydrobromide, hydriodide, phosphate, nitrate, sulfate, acetate, citrate, gluconate, benzoate, hibenzate[2-(4-hydroxybenzoyl)benzoate], fendizoate(2-[(2'-hydroxy-4-biphenylyl)carbonyl]benzoate), propionate, butyrate, sulfosalicylate, maleate, laurate, malate, fumarate, succinate, oxalate, tartrate, amsonate(4,4'-diaminostilbene-2,2'-disulfonate), embonate[4,4'-methylene-bis-(3-hydroxy-2-naphthoate)], metembonate[4,4'-methylene-bis-(3-methoxy-2-naphthoate)], stearate, tosylate(p-toluenesulfonate), 2-hydroxy-3-naphthoate, 3-hydroxy-2-naphthoate and mesylate(methanesulfonate).

One embodiment of the invention comprises substituted 1-phenyl-2-pyrrolidin-2-yl-ethanols (b) of formula I, wherein
  $R^1$ denotes a hydrogen atom (—H) or alkyl with from 1 to 3 carbon atoms,
  $R^2$ denotes hydroxyl, methyl or methoxy, and
  $R^7$ denotes a hydrogen atom,
and their acid-addition salts.

A preferred embodiment of the invention comprises those substituted 1-phenyl-2-pyrrolidin-2-yl-ethanols (c) of formula I,
wherein
$R^1$ denotes a hydrogen atom or methyl,
$R^2$ denotes methyl or methoxy, and
$R^7$ denotes a hydrogen atom,
and their pharmacologically-compatible acid-addition salts.

Representative compounds according to the invention are, for example:
1-(3-chlorophenyl)-2-pyrrolidin-2-yl-ethanol,
1-(3-isopropoxyphenyl)-2-(1-methylpyrrolidin-2-yl)-ethanol,
1-(3-ethylphenyl)-2-(1-ethylpyrrolidin-2-yl)-ethanol,
1-(3-hydroxyphenyl)-2-(1-isopropylpyrrolidin-2-yl)-ethanol,
1-[3-(n-butoxy)phenyl]-2-[1-(n-heptyl)pyrrolidin-2-yl]-ethanol,
1-[3-(tert.-butyl)phenyl]-2-(1-methylpyrrolidin-2-yl)-ethanol,
1-(3-ethoxyphenyl)-2-[1-(n-hexyl)pyrrolidin-2-yl]-ethanol, and
1-(3-chlorophenyl)-2-(1-methylpyrrolidin-2-yl)-ethanol,
heptanoic acid-[1-(3-methoxyphenyl)-2-(1-methylpyrrolidin-2-yl)-ethyl]-ester,
isobutyric acid-[1-(3-methoxyphenyl)-2-(1-methylpyrrolidin-2-yl)-ethyl]-ester,
propionic acid-[1-(3-methoxyphenyl)-2-(1-isopropylpyrrolidin-2-yl)-ethyl]-ester,
2-[1-(3-methoxyphenyl)-2-(1-isobutylpyrrolidin-2-yl)-ethoxy]-tetrahydropyrane,
2-[2-isopropoxy-2-(3-methoxyphenyl)-ethyl]-1-methylpyrrolidine,
2-[2-hexyloxy-2-(3-methoxyphenyl)-ethyl]-1-methylpyrrolidine, preferably
1-(3-methoxyphenyl)-2-pyrrolidin-2-yl-ethanol,
2-(1-methylpyrrolidin-2-yl)-1-(m-tolyl)ethanol,
1-(3-methoxyphenyl)-2-(1-methylpyrrolidin-2-yl)-ethanol, and their acid-addition salts.

The substituted 1-phenyl-2-pyrrolidin-2-yl-ethanols of formula I possess a chirality center at each carbon atom marked with (*). The invention therefore includes diastereoisomers, racemates, enantiomers and all mixtures of the foregoing. In the designation of the configuration of the stereo-isomers, the rule that is followed is that of R. S. Cahn, C. K. Ingold and V. Prelog [cf. *Angew. Chem.*, 78 (1966) 413] or IUPAC Tentative Rules for the Nomenclature of Organic Chemistry, Sect. E, Fundamental Stereo-chemistry, *J. Org. Chem.*, 35 (1970) 2849, or *Chemical Abstracts*, Stereochemical Nomenclature of Organic Substances in the Ninth Collective Period (1972–1976), or *J. Chem. Inf. Comput. Sci.*, 15 (1975) 67.

The substituted 1-phenyl-2-pyrrolidin-2-yl-ethanols of formula I and the pharmacologically-, i.e. biologically-, compatible acid-addition salts possess valuable properties which make them commercially exploitable. They exhibit a strong analgesic action. Further, they are characterized by low toxicity and absence of significant side-effects. A further advantage of the compounds according to the invention is that they cause neither dependence (addition) nor tolerance development (adaptation).

The excellent and specific effectiveness of the substituted 1-phenyl-2-pyrrolidin-2-yl-ethanols of formula I makes their use possible both in human and in veterinary medicine; they are used for the prophylaxis of complaints or, more particularly, for treatment of symptoms which have already occurred.

As indications for the human medical range these compounds are useful, for example, for treating men, woman or children, for treating acute or chronic pain conditions of various etiology, for example post-operative pain, pain resulting from injury, chemical or other burns, spasmodic pain (e.g. in colics) in the biliary or urinary tract, chronic pain in bone and joint diseases and in neuralgias, pain in diagnostic and therapeutic operations and after birth.

In the field of veterinary medicine similar pain conditions are also treated in, e.g., higher animals, such as economically-useful animals and domestic animals.

The invention also includes medicaments which contain the substituted 1-phenyl-2-pyrrolidin-2-yl-ethanols of formula I and/or their pharmacologically-compatible acid-addition salts.

Preferred medicaments are those which contain the substituted 1-phenyl-2-pyrrolidin-2-yl-ethanols (b) and (c), particularly (c), and/or their pharmacologically-compatible acid-addition salts.

The medicaments are prepared according to processes known per se. As medicaments, the compounds according to the invention are used either as such or, preferably, in combination with suitable pharmaceutical excipients, carriers, fillers or other additives. If the new pharmaceutical preparations contain pharmaceutical excipients in admixture with or otherwise in addition to the compounds according to the invention, the content of active substance is from 0.5 to 95, preferably from 15 to 75, percent by weight of the total preparation.

In the human and veterinary medical fields the active substances are applied in any suitable form with the proviso that the formation or maintenance of sufficient active-substance levels is ensured. That is achieved, for example, by oral, rectal or parenteral (intravenous, intramuscular, subcutaneous) administration in suitable doses. Advantageously, the pharmaceutical preparation of the active substance in unitary-dose form is matched to the desired mode of administration. A unitary dose may, for example, be a tablet, a dragée, a capsule, a suppository or a measured volume amount of a powder, a granulate, a solution, an emulsion or a suspension.

A "unitary dose" in the sense of the present invention is a physically-specified unit which contains an individual amount of the active constituent in combination with a pharmaceutical excipient and whose active-substance content corresponds to a fraction or multiple of a therapeutic single dose. A single dose preferably contains the amount of active substance which is administered in one application and which usually corresponds to a whole, a half, a third or a quarter of the daily dose. If, for a single therapeutic administration, only a fraction, such as the half or a quarter, of the unitary dose is required, the unitary dose is advantageously divisible, e.g., in the form of a tablet with a break score.

The pharmaceutical preparations according to the invention contain, when they are present in unitary doses and are intended for application, e.g., to humans, from about 0.1 to 250 mg, advantageously from 1.0 to 100 mg and, in particular, from 5 to 50 mg of active substance.

In general, it is expedient in human medicine to administer the active subtance(s), in the case of oral administration, in a daily dose of from about 0.01 to about 5, preferably from 0.1 to 3, mg/kg of body weight, possibly in the form of several, preferably 1 to 3, individual doses in order to achieve the desired results. An individual dose contains the active substance(s) in amounts of from about 0.01 to about 2.5, preferably from 0.1 to 1.5, mg/kg body weight. In the case of a parenteral, e.g. intravenous, treatment, corresponding dosages are used.

The therapeutic administration of the pharmaceutical preparation is effected 1 to 4 times daily at fixed or varying points in time, e.g. in each case after meals and/or in the evening. It may, however, be necessary to deviate from the said dosages, depending on the nature, the body weight and the age of the subject to be treated, the nature and the gravity of the illness, the nature of the preparation and of the application of the medicament, as well as the period or interval within which the administration is effected. Thus, in the case of chronic pain conditions, it may suffice to manage with smaller amounts of active substance whereas, in serious cases of acute pain conditions, the above-mentioned amounts of active substance may, without misgivings, be exceeded for short periods.

The fixing of the respectively necessary optimum dosage and type of application of the active substances is effected by the expert on the basis of his specialized knowledge.

The pharmaceutical preparations preferentially consist of active substance according to the invention and non-toxic, pharmaceutically-compatible medicament excipient, (and/or carrier, filler or other pharmacologically-acceptable additive), which is used in admixture with or as diluent for the active substance; the excipient is in solid, semi-solid or liquid form or as enveloping agent, for example in the form of a capsule, a tablet coating, a bag or another container for the therapeutically-active constituent. An excipient may serve, e.g., as intermediary for the uptake of the medicament by the body, as formulation auxiliary, as sweetener, as taste corrigent, as coloring matter or as preservative.

Tablets, dragées, hard and soft capsules (e.g. of gelatin), dispersible powders, granulates, aqueous and oily suspensions, emulsions, solutions or syrups are illustrative of medicament forms suitable for oral administration.

Tablets ordinarily contain inert diluents, e.g. calcium carbonate, calcium phosphate, sodium phosphate, or lactose; granulation and distribution agents, e.g. maize starch or alginates; binders, e.g. starch, gelatin or acacia gum; and lubricants, e.g. aluminum stearate, magnesium stearate, talc or silicone oil. If desired, they may additionally be provided with a coating which is optionally of such a nature that it causes delayed dissolving and absorption of the medicament in the gastro-intestinal tract and thus, e.g., better compatibility, protraction or retardation is achieved. Gelatin capsules generally contain the medicament mixed with a diluent, e.g. a solid diluent, such as calcium carbonate or kaolin, or an oily diluent, such as neutral oil, olive oil, arachis oil or paraffin oil.

Aqueous suspensions optionally contain suspending agents, e.g. sodium carboxymethyl cellulose, methyl cellulose, hydroxypropyl cellulose, sodium alginate, polyvinylpyrrolidone, gum tragacanth or acacia gum; dispersing and wetting agents, e.g. polyoxyethylene stearate, heptadeca-ethyleneoxycetanol, polyoxyethylenesorbitol mono-oleate, polyoxyethylenesorbitan mono-oleate or lecithin; preservatives, e.g. methyl or propyl hydroxybenzoates; flavoring; sweetener, e.g. sucrose, lactose, sodium cyclamate, dextrose or invert sugar syrup.

Oily suspensions contain, e.g., arachis, olive, sesame, coconut or paraffin oil and thickener, such as beeswax, hard paraffin or cetyl alcohol, as well as sweetener, flavoring and anti-oxidant.

Emulsions contain, e.g., olive, arachis or paraffin oil besides emulsifying agent (such as acacia gum, gum tragacanth, phosphatide, sorbitan mono-oleate or polyoxyethylenesorbitan mono-oleate), sweetener and flavoring.

For rectal application of the medicament, suppositories (prepared with the use of binder which melts at rectal temperature, for example cocoa butter or polyethylene glycol) are used.

For parenteral application of the medicament, aqueous solutions or suspensions (capable of being injected in sterile manner, e.g. isotonic salt solutions or other solutions which contain dispersing or wetting agents and/or pharmacologically-compatible diluents, e.g. propylene or butylene glycol) are suitable.

In addition to the new compounds according to the invention the pharmaceutical preparations, which are conventionally prepared, optionally also contain one or more physically-, chemically- and physiologically-compatible pharmacologically-active constituents from other groups of medicaments, for example antipyretics, analgesics, antiphlogistic agents (e.g. phenylbutazone, bumadizon, phenacetin, indomethacin and lonazolac), hypnotics (such as barbiturates, e.g. hexobarbital and vinylbarbital), stimulants (e.g. caffeine), sedatives (such a meprobamate and benzodiazepines, e.g. diazepam, oxazepam and chlorodiazepoxide), spasmolytics (such as papaverine), vitamins (e.g. vitamin $B_1$, vitamin $B_6$, vitamin $B_{12}$, vitamin C, vitamin $B_1$ chloride hydrochloride, vitamin $B_6$ hydrochloride and cyanocobalamin).

A further aspect of the invention is a process for the treatment of mammals which suffer from pain conditions; it is characterized by administering to a pain-afflicted mammal an analgesically-effective and pharmacologically-compatible dose of one or more substituted 1-phenyl-2- 2-yl-ethanols and/or of its or their pharmacologically-compatible acid-addition salts.

The invention also includes a process for the preparation of the substituted 1-phenyl-2-pyrrolidin-2-yl-ethanols of formula I and of the acid-addition salts thereof. Such process is characterized in that a substituted 1-phenyl-2-pyrrolidin-2-yl-ethanone of one of the formulae:

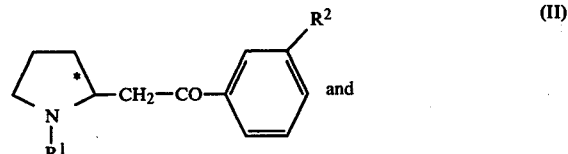

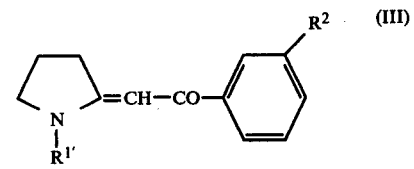

wherein
$R^1$ and $R^2$ have their previously-ascribed meanings, and $R^{1'}$ denotes alkyl with from 1 to 7 carbon atoms, or an acid-addition salt thereof is reduced and, where appropriate, subsequently acylated or etherified and/or, where appropriate or desired, the obtained free base is conventionally converted into a corresponding acid-addition salt, or the obtained acid-addition salt is conventionally converted into its corresponding free base or into a different acid-addition salt.

The reduction of the substituted 1-phenyl-2-pyrrolidin-2-yl-ethanones of formulae II and III is effected according to processes known per se to one skilled in the art. When starting compounds III are used, the reduction is carried out in one or two steps. Because of the ease of conducting reactions and more favorable yields, the two-step process is preferred to the one-step process.

For the reduction of the keto group in the starting compounds II, suitable reducing agents are, e.g., reducing complex metal hydrides, such as lithium hydridoaluminate (=lithium aluminum hydride), in an ether, such as diethyl ether or tetrahydrofuran, or sodium hydridoborate (=sodium borohydride) in alcohol, such as methanol, ethanol, isopropanol and their mixtures with one another and with water. The reduction is preferably carried out with sodium hydridoborate. The reaction takes place at temperatures between 0° and 80° C. with reaction times of from 10 minutes to 6 hours. Expediently, the reaction is carried out at temperatures around 0° C. in a suitable solvent through portion-wise addition of the reducing agent, the temperature of the solution rising gradually to room temperature. After completion of the reaction, the reaction mixture is worked up in the usual manner through treatment with water. The reduction is alternatively effected with hydrogen in the presence of a suitable catalyst, such as Raney nickel, platinum, platinum on activated charcoal, etc., at from 0° to 80° C. and at pressures of from 1 to 500 atmospheres.

When the reaction is conducted in two steps, the starting compounds III are first reduced to obtain the compounds II; suitable reducing agents for this purpose are, for example, lithium hydridoaluminate or sodium dihydridobis-(2-methoxyethoxy)aluminate. The reaction takes place in a usual solvent, such as an ether, e.g. diethyl ether and tetrahydrofuran, or a hydrocarbon, e.g. benzene and toluene, at from −20° to 60° C. and, preferably, between 0° C. and room temperature, with reaction times of from 10 minutes to 10 hours. The reaction is preferably effected in tetrahydrofuran at a temperature of around 0° C. with portionwise addition of lithium aluminum hydride; the reaction in general is complete after half an hour. Further reduction of obtained compounds II is then effected according to the previously-described process.

When the reaction is conducted in one step, the reduction of starting compounds III is effected, e.g., with lithium hydridoaluminate or sodium dihydrido-bis-(2-methoxyethoxy)aluminate in an ether, such as diethyl ether and tetrahydrofuran, or with sodium borohydride in an alcohol, such as methanol, ethanol and propanol, or in an alcohol-water mixture at temperatures of from 20° C. to the boiling temperature of the solvent; the reducing agent is used in an excess. The reaction time is from 1 to 48 hours.

An optionally following acylation of the hydroxy group is effected according to processes known per se to one skilled in the art, for example by reaction with the suitable carboxylic acid anhydrides or carboxylic acid chlorides, optionally in the presence of a proton acceptor, e.g. an alcali metal carbonate or a tertiary amine, such as pyridine or triethylamine. The reaction may be carried out in an inert solvent, such as benzene, cyclohexane, diethylether or methylene chloride.

The optionally following etherification is effected e.g. by reaction with alkyl halides, such as alkyl iodides, in inert solvents, e.g. dimethyl formamide, toluene, tetrahydrofurane, in the presence of a strong base, such as potassium hydroxide or sodium hydride. The tetrahydropyranyl ether can be synthesized by reaction with dihydropyrane in the presence of an acid catalyst, e.g. sulfonic acids, such as p-toluene sulfonic acid.

Acid-addition salts are obtained by dissolving the free base in a suitable solvent, such as acetone, water or a low-molecular-weight aliphatic alcohol (e.g. ethanol and isopropanol), which contains the desired acid or to which the desired acid is subsequently added. The salts are recovered by filtration, precipitation with a non-solvent for the addition salt or by evaporation of the solvent.

Obtained salts, e.g. the hydrochlorides, are converted into the free base by neutralization with aqueous sodium or potassium hydroxide; the free base is then recovered by solvent extraction with a suitable water-immiscible solvent, such as chloroform, dichloromethane, diethyl ether, benzene, toluene or cyclohexane. The free bases are also optionally obtained, e.g., by neutralization of an acid-addition salt with sodium methylate in methanol and isolation of the base according to known processes.

Diastereoisomers and racemates are conventionally separated. The separation of diastereoisomers is effected, e.g., on the basis of their different physical-chemical properties, such as melting point and solubility; the separation of racemates into their optically-active isomers is effected with the aid of optically-active splitting agents, e.g. optically-active acids, such as tartaric acid, dibenzoyltartaric acid, camphorsulfonic acid and desoxycholic acid. Racemic mixtures are also separated into the optical isomers through chromatography via optically-active sorbing agents.

The ethanones of formula II, used as starting compounds, are obtained according to processes which are known per se. For example, ethanones II in which $R^1$ denotes a hydrogen atom are prepared through condensation of pyrroline-1 with appropriate 3-substituted acetophenones and methyl magnesium carbonate according to a process described by J. M. Grisar et al [Synthesis, 1974, 284; J. Med. Chem., 19 (1976) 1195]; they are converted through N-alkylation into ethanones II in which $R^1$ denotes an alkyl group with from 1 to 7 carbon atoms. The N-alkylation is effected with conventional alkylating agents, such as alkyl halides (e.g. ethyl iodide), alkyl sulfonates (e.g. methyl tosylate) and alkyl sulfates (e.g. dimethyl sulfate), in an inert solvent, such as a ketone (e.g. acetone and ethyl methyl ketone), or an alcohol (e.g. methanol, ethanol and isopropanol), or without solvent and with addition of an auxiliary base, such as sodium carbonate, potassium carbonate, pyridine or triethylamine.

The starting compounds of formula III are prepared according to various processes. For example, they are obtained through reaction of 1-alkyl-2-alkoxypyrrolidines of formula IV with appropriate 3-substituted acetophenones V according to the reaction scheme:

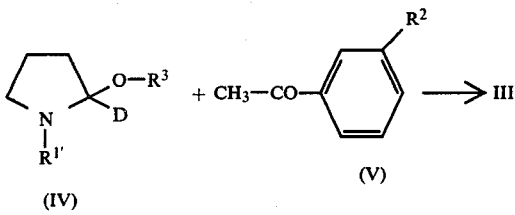

wherein
R¹' and R² have their previously-ascribed meanings,
D denotes —O—R⁴ or —N(R⁵)R⁶,
R³, R⁴, R⁵ or R⁶ are the same or different and denote alkyl with from 1 to 5 carbon atoms, preferably ethyl or methyl.

The reaction takes place in the absence or presence of basic catalyst, such as triethylamine or 1,5-diazabicyclo-[5,4,0]undec-5-ene, at temperatures from room temperature to 100° C. without solvent or in inert solvent, such as benzene, toluene or methylene chloride.

The starting compounds of formula III are alternatively obtained through reaction of pyrrolinium salts VI with appropriate 3-substituted acetophenones V according to the reaction scheme:

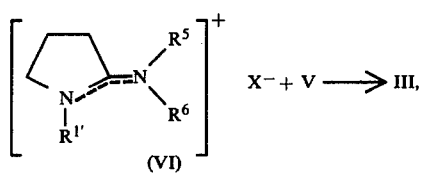

wherein
R¹', R⁵ and R⁶ have their previously-ascribed meanings, and
X⁻ stands for an equivalent of an anion of an organic or inorganic acid.

The reaction takes place in an inert solvent, such as an alcohol (e.g. methanol, ethanol, isopropanol, butanols and pentanols), in the presence of a strong base, such as an alkali metal alcoholate (e.g. sodium methanolate, sodium ethanolate, potassium propanolate, potassium tert.-butanolate and potassium tert.-pentanolate), at temperatures of from 20° to 150° C., preferably of from 80° to 100° C.

The 1-alkyl-2-alkoxypyrrolidines IV are obtained by reacting salts of formula VI with alkali-metal alcoholates, such as sodium methanolate or ethanolate in a suitable solvent [along the lines of H. Bredereck et al., Chem. Ber., 97 (1964) 3081; Chem. Ber., 98 (1965) 1078]. Preferred solvents (for preparing pyrrolidines IV in which D denotes an —O—R⁴ group) are alcohols R⁴-OH, in which R⁴ has its previously-noted meaning; preferred solvents [for preparing pyrrolidines IV in which D denotes -N(R⁵)R⁶] are inert solvents, such as benzene and ethers, e.g. diethyl ether.

Preparation of salts VI is effected in analogy with H. Bredereck et al. [Chem. Ber., 97 (1964) 3081] through reaction of an appropriate N-substituted 2-pyrrolidinone with an alkylating agent, such as diethyl sulfate, methyl iodide or, preferably, dimethyl sulfate, in an inert solvent at from room temperature to 120° C., preferably without solvent at temperatures around 80° C., and subsequent reaction with an amine HN(R⁵)R⁶, in which R⁵ and R⁶ have their previously-noted meanings, or through reaction of an appropriate N-substituted pyrrolidinone with an inorganic acid chloride, such as phosphorus oxide trichloride or phosgene, and subsequent reaction with an amine HN(R⁵)R⁶ (in which R⁵ and R⁶ have their previously-noted meanings) in inert solvent, such as benzene, at temperatures between 0° and 100° C., preferably at from 20° to 60° C., or without solvent at temperatures between 0° and 100° C., preferably at from 40° to 80° C.

The following examples illustrate the invention more fully without restricting it. m.p. denotes melting point; b.p. denotes boiling point; and stated temperatures are in °C.

EXAMPLE 1

2-dimethylamino-1-methyl-1-pyrrolinium methyl sulfate 22.5 g of 2-methoxy-1-methyl-1-pyrrolinium methyl sulfate are added dropwise (with stirring) to a solution of 6.76 g of dimethylamine in 45 ml of benzene. The resulting admixture is subsequently boiled under reflux for 1 hour. The obtained heavy phase is separated off, extracted twice by shaking with diethyl ether and freed from solvent residues in a vacuum. 19.4 g (81.4% of theory) of the title compound (as a red-brown oil) are thus obtained.

EXAMPLE 2

1-isopropyl-2-methoxy-1-pyrrolinium methyl sulfate 89.6 g of 1-isopropylpyrrolidinone-2 and 88.9 g of dimethyl sulfate are stirred for 3 hours at 80°. The reaction mixture is extracted 5 times with, in each case, 50 ml of diethyl ether and the obtained red oil is dried under a high vacuum to yield 167.2 g (94% of theory) of the title compound.

Thin-layer chromatography: layer silica gel neutral solvent system chloroform/methanol 9:1, $R_F$ value 0.30 color reagent: iodine vapor

EXAMPLE 3

2-dimethylamino-1-isopropyl-1-pyrrolinium methyl sulfate 161 g of 1-isopropyl-2-methoxy-1-pyrrolinium methyl sulfate are added dropwise, with stirring, to a solution of 43.8 g of dimethylamine in 283 ml of benzene. Subsequently, boiling under reflux is effected for 1.5 hours; the heavy phase is separated off and washed 4 times with, in each case, 50 ml of diethyl ether. After drying under a high vacuum, 154 g (91% of theory) of the title compound (as a reddish oil) are obtained.

EXAMPLE 4

1-(3-methoxyphenyl)-2-(1-methyl-2-pyrrolidinyliden)ethanone

A solution of 10.35 g of sodium in 225 ml of ethanol is added dropwise at 90° (with stirring) in the course of one hour to a mixture of 107 g of 2-dimethylamino-1-methyl-1-pyrrolinium methyl sulfate and 45.1 g of 3-methoxyacetophenone; stirring is effected for a further 2 hours at this temperature, and the solvent is then largely distilled off under a vacuum. 300 ml of water and 300 ml of diethyl ether are added to the cooled residue, and thorough shaking is effected. The ethereal phase is collected, dried over sodium sulfate and concentrated. The crystalline residue is recrystallized from chloroform/cyclohexane to yield 41.8 g of the title compound (as yellowish crystals), m.p. 92° to 93°.

EXAMPLE 5

2-(1-isopropyl-2-pyrrolidinylidene)-1-(3-methoxyphenyl)ethanone

A solution of 7.6 g of sodium in 100 ml of ethanol is added dropwise(*) at 90° within 2 hours to a mixture of 88 g of 1-isopropyl-2-dimethylamino-1-pyrrolinium methyl sulfate and 42 g of 3-methoxyacetophenone. Stirring is continued for a further 4 hours at this temperature; the solvent is distilled off in a vacuum; and the residue is distributed in 250 ml of dichloromethane and 250 ml of water. The organic phase is collected, dried over sodium sulfate and concentrated. The oil remaining behind is freed from excess 3-methoxyacetophenone by heating under a high vacuum. Yield: 42.8 g (59% of theory) of the title compound as brown oil.
(*)with stirring

EXAMPLE 6

1-(3-methylphenyl)-2-(1-methyl-2-pyrrolidinyliden)ethanone

Following the procedure of Example 4, 84.7 g (53 percent of theory) of the title compound, m.p. 60° to 62° (from cyclohexane), are obtained from 100 g of 3-methylacetophenone, 238.3 g of 2-dimethylamino-1-methyl-1-pyrrolinium methyl sulfate and a solution of 23 g of sodium in 500 ml of ethanol.

EXAMPLE 7

1-(3-chlorophenyl)-2-(1-methyl-2-pyrrolidinyliden)ethanone

Following the procedure of Example 4, 39.0 g (51 percent of theory) of the title compound are obtained as brown oil from 50 g of 3-chloro-acetophenone, 103 g of 2-dimethylamino-1-methyl-1-pyrrolinium methyl sulfate and a solution of 9.9 g of sodium in 130 ml of ethanol.

EXAMPLE 8

1-(3-methoxyphenyl)-2-(1-methyl-2-pyrrolidinyl)ethanone 11.8 g of lithium aluminum hydride are added portionwise at 0° with stirring to 144.8 g of 1-(3-methoxyphenyl)-2-(1-methyl-2-pyrrolidinyliden)ethanone dissolved in 1.4 liters of tetrahydrofuran. 30 minutes after completion of the addition, 300 ml of water are cautiously added dropwise, with cooling; then 800 ml of diethyl ether are added, and the organic phase is collected. The organic phase is dried over sodium sulfate, the solvent is removed by evaporation, and the oily residue is distilled under a vacuum to obtain 127 g (87% of theory) of the title compound:
b.p. 115° at 0.01 mm Hg. Picrate (from ethanol): m.p. 153° to 156°.

EXAMPLE 9

1-(3-methylphenyl)-2-(1-methyl-2-pyrrolidinyl)ethanone 5.8 g of lithium aluminum hydride are added portionwise at 0° to 66 g of 1-(3-methylphenyl)-2-(1-methyl-2-pyrrolidinyliden)ethanone dissolved in 550 ml of tetrahydrofuran. 20 minutes after completion of the addition, water is added dropwise until no evolution of gas is any longer observed. The light-yellow organic phase is decanted from the formed precipitate, the latter is extracted with diethyl ether, the united organic phases are dried over sodium sulfate and concentration to an oil is effected. After distillation under vacuum, 61.7 g (92% of theory) of the title compound (b.p. 116° at 0.01 mm Hg) are obtained. Picrate (from ethanol): m.p. 146° to 149°.

EXAMPLE 10

2-(1-isopropyl-2-pyrrolidinyl)-1-(3-methoxyphenyl)ethanone

Following the procedure of example 8, 24.8 g (64% of theory) of the title compound (b.p. 120° to 123° at 0.01 mm Hg) are obtained from 38.8 g of 2-(1-isopropyl-2-pyrrolidinylidene)-1-(3-methoxyphenyl)-ethanone.

EXAMPLE 11

1-(3-methoxyphenyl)-2-(1-methyl-2-pyrrolidinyl)ethanol 50 g of 1-(3-methoxyphenyl)-2-(1-methyl-2-pyrrolidinyl)ethanone are dissolved in 100 ml of methanol and 20 ml of water; thereafter, 4.05 g of sodium borohydride are added portionwise, with stirring. Stirring is continued for a further hour, methanol is largely distilled off, 100 ml of water are added and extraction is effected with methylene chloride. The organic phase is extracted with 400 ml of 10% strength hydrochloric acid, the hydrochloric acid aqueous phase is rendered alkaline with sodium hydroxide solution and the liberated base is extracted with methylene chloride. The organic phase is concentrated and the resulting oily residue is distilled to obtain 47.4 g (94% of theory) of the title compound as a mixture of diastereoisomers of b.p. 128° at 0.001 mm Hg.

EXAMPLE 12

(R*,S*)-1-(3-methoxyphenyl)-2-(1-methyl-2-pyrrolidinyl)ethanol 45 g of the mixture of diastereoisomers of Example 11 are dissolved hot in 100 ml of cyclohexane, and 100 ml of low-boiling petroleum ether are added thereto. The resulting mixture is left to stand overnight at 0°, and precipitated crystals (21 g) are filtered off. Recrystallization from 100 ml of cyclohexane/petroleum ether (1:1) yields 14.4 g of the title compound: m.p. 79° to 82°.

Through reaction of the base with an equivalent amount of acid, the following salts are obtained:
maleate, colorless oil, oxalate, colorless oil, fumarate, colorless oil, embonate, yellow oil, benzoate, colorless oil.

EXAMPLE 13

(R*,R*)-1-(3-methoxyphenyl)-2-(1-methyl-2-pyrrolidinyl)ethanol

The filtrate obtained in Example 12 is concentrated to a colorless oil. The oil is dissolved in 50 ml of methanol, and ethereal hydrochloric acid is slowly added thereto; 12.1 g of the hydrochloride of the title compound precipitate and are recrystallized from methanol/diethyl ether (m.p. 136° to 139°).

EXAMPLE 14

2-(1-isopropyl-2-pyrrolidinyl)-1-(3-methoxyphenyl)ethanol

Following the procedure of Example 11, 15.9 g of the title compound (as a mixture of diastereoisomers): b.p. 130° to 132° at 0.03 mm Hg, are obtained from 23.6 g of 2-(1-isopropyl-2-pyrrolidinyl)-1-(3-methoxyphenyl)ethanone and 3.5 g of sodium borohydride.

EXAMPLE 15

1-(3-methylphenyl)-2-(1-methyl-2-pyrrolidinyl)ethanol

Following the procedure of Example 11, 23.4 g (77% of theory) of the title compound (as a mixture of diastereosiomers): b.p. 105° at 0.008 mm Hg, which soon partially crystallizes, are obtained from 30 g of 1-(3-methylphenyl)-2-(1-methyl-2-pyrrolidinyl)ethanone and 5.24 g of sodium borohydride.

EXAMPLE 16

(R*,S*)-1-(3-methylphenyl)-2-(1-methyl-2-pyrrolidinyl)ethanol 17 g of the diastereoisomers of Example 15 are recrystallized from 60 ml of petroleum ether (b.p. 50° to 70°). The crude product so obtained is again recrystallized from petroleum ether. 3.5 g of the title compound: m.p. 78° to 80°, are thus obtained.

EXAMPLE 17

(R*,R*)-1-(3-methylphenyl)-2-(1-methyl-2-pyrrolidinyl)ethanol

The first filtrate obtained in Example 16 is concentrated to a colorless oil, which is distilled under a high vacuum. 6.0 g of the title compound are thus obtained as colorless oil: b.p. 105° at 0.008 mm Hg.

EXAMPLE 18

1-(3-hydroxyphenyl)-2-(1-methyl-2-pyrrolidinyl)ethanone 40.5 of 1-(3-methoxyphenyl)-2-(1-methyl-2-pyrrolidinyl)ethanone are boiled under reflux for 6 hours with 180 ml of acetic acid and 180 ml of 47% hydrobromic acid. After concentration of the solution, the oily residue is brought to crystallization through treatment with 150 ml of hot ethanol. Cooling is allowed to take place, and 39.8 g (76% of theory) of the hydrobromide of the title compound is filtered off as greenish crystals: m.p. 165° to 168°.

EXAMPLE 19

1-(3-hydroxyphenyl)-2-(1-methyl-2-pyrrolidinyl)ethanol

Following the procedure of Example 11, 3.0 g of the title compound (as a mixture of diastereoisomers) in the form of a yellow viscous oil [from which a crystalline diastereoisomer (m.p. 147° to 150°) is isolated after recrystallization from ethanol] are obtained from 4.5 g of 1-(3-hydroxyphenyl)-2-(1-methyl-2-pyrrolidinyl)ethanone hydrobromide and 1.0 g of sodium borohydride.

EXAMPLE 20

1-(3-methoxyphenyl)-2-(2-pyrrolidinyl)ethanone 60 ml of a 2-molar solution of methyl magnesium carbonate in dimethylformamide are heated to 120° in a carbon dioxide stream. 5 g of 3-methoxyacetophenone are added; stirring under nitrogen is effected for 4 hours at this temperature, followed by cooling, and 2.5 g of 3,4-dihydro-2H-pyrrole are added. Stirring is effected for 2 days in a carbon dioxide stream, followed by pouring onto a mixture of 25 ml of concentrated hydrochloric acid and 150 g of ice and extraction with dichloromethane. After drying over sodium sulfate, the organic phase is concentrated and the hydrochloride of the title compound (7.5 g) is obtained as yellow oil, which is triturated with 150 ml of diethyl ether for about 30 minutes. The resulting precipitate is recrystallized from 200 ml of methanol/diethyl ether (1:4), thus yielding colorless crystals (m.p. 140° to 142°).

EXAMPLE 21

2-[1-(n-hexyl)-2-pyrrolidinyl]-1-(3-methoxyphenyl)ethanone 5.11 g of 1-(3-methoxyphenyl)-2-(2-pyrrolidinyl)ethanone hydrochloride, 5.6 g of anhydrous potassium carbonate, 3.7 g of 1-bromohexane and 60 ml of ethyl methyl ketone are heated under reflux for 18 hours. The solvent is distilled off, the residue is taken up with 50 ml of water and extraction is effected twice with, in each case, 50 ml of diethyl ether. After drying over sodium sulfate, the united organic phases are concentrated to an oil, which is distilled under a high vacuum to obtain 5.0 g (82% of theory) of the title compound: b.p. 138° to 144° at 0.005 mm Hg.

EXAMPLE 22

2-[1-(n-hexyl)-2-pyrrolidinyl]-1-(3-methoxyphenyl)ethanol

Following the procedure of Example 11, 3.5 g (87% of theory) of the title compound (as an oily mixture of diastereoisomers): b.p. 138° to 140° at 0.005 mm Hg, are obtained from 4.0 g of 2-[1-(n-hexyl)-2-pyrrolidinyl]-1-(3-methoxyphenyl)ethanone and 0.5 g of sodium borohydride.

EXAMPLE 23

1-(3-chlorophenyl)-2-(1-methyl-2-pyrrolidinyl)ethanone

Following the procedure of Example 9, 21 g of the title compound: b.p. 112° at 0.005 mm Hg, are obtained from 35 g of 1-(3-chlorophenyl)-2-(1-methyl-2-pyrrolidinyliden)ethanone and 2.83 g of lithium aluminum hydride.

EXAMPLE 24

1-(3-chlorophenyl)-2-(1-methyl-2-pyrrolidinyl)ethanol

Following the procedure of Example 11, 12.1 g of the title compound (as a mixture of diastereoisomers): b.p. 120° to 125° at 0.005 mm Hg, are obtained from 15 g of 1-(3-chlorophenyl)-2-(1-methyl-2-pyrrolidinyl)ethanone and 1.2 g of sodium borohydride.

EXAMPLE 25

Repeating the procedure of Examples 1, 4, 8, 10 and 11, the following compounds of formula I (as a mixture of diastereoisomers) are obtained from equivalents of corresponding starting materials:
1-(3-propylphenyl)-2-(1-propyl-2-pyrrolidinyl)ethanol,
2-[1-(n-butyl)-2-pyrrolidinyl]-1-(3-isopropylphenyl)ethanol,
1-[3-(sec.-butyl)phenyl]-2-[1-(n-pentyl)-2-pyrrolidinyl]ethanol.

EXAMPLE 26

2-[2-methoxy-2-(3-methoxyphenyl)-ethyl]-1-methylpyrrolidine 1.0 g of 1-(3-methoxyphenyl)-2-(1-methyl-2-pyrrolidinyl)-ethanol dissolved in 15 ml of dimethyl formamide is added dropwise within 5 minutes, with stirring and exclusion of moisture, to a suspenion of 0.25 g of 80 p.c. sodium hydride. Stirring is effected for 30 minutes and a solution of 0.85 g methyl iodide in 10 ml of dimethyl formamide is added drop by drop. The mixture is kept at 60° for 2 hours, treated with water and extracted with diethyl ether. The etheral phase is concentrated. There are obtained 0.7 g of the title compound as oily mixture of diastereoisomers.

EXAMPLE 27

2-[1-(3-methoxyphenyl)-2-(1-methylpyrrolidin-2-yl)-ethoxy]tetrahydropyran 0.3 g of (R*,R*)-1-(3-methoxyphenyl)-2-(1-methyl-2-pyrrolidinyl)-ethanol-hydrochloride, one drop of etheral hydrochloric acid and 3.5 ml of 3.4-dihydro-2H-pyran are stirred for 24 hours at room temperature and subsequently concentrated to 0.39 g of the oily hydrochloride of the title compound.

EXAMPLE 28

(R*,S*)-acetic acid-[1-(3-methoxyphenyl)-2-(1-methyl-2-pyrrolidinyl)-ethyl]-ester 3,5 g of (R*,S*)-1-(3-methoxyphenyl)-2-(1-methyl-2-pyrrolidinyl)-ethanol and 40 ml of acetic acid anhydride are stirred for 15 minutes at room temperature. 6 N sodium hydroxide solution is added with cooling up to a pH of 8-9. The mixture is extracted with diethyl ether, and the organic layer is concentrated to the oily title compound. The hydrochloride (from methanol/diethyl ether) melts at 155°-157°.

EXAMPLE 29

(R*,R*)-acetic acid-[1-(3-methoxyphenyl)-2-(1-methyl-2-pyrrolidinyl)-ethyl]-ester According to the method of working described in Example 28, from 3.0 g of (R*,R*)-1-(3-methoxyphenyl)-2-(1-methyl-2-pyrrolidinyl)-ethanol and 30 ml of acetic acid anhydride there are obtained 1.56 g of the title compound as tough, colourless oil of b.p. 130° at 0.008 mm Hg.

EXAMPLE 30

1-hexanoic acid-[1-(3-methoxyphenyl)-2-(1-methyl-2-pyrrolidinyl)-ethyl]-ester

A solution of 0.7 g of hexanoyl chloride in 10 ml of methylene chloride is added drop by drop to a mixture of 1.17 g of 1-(3-methoxyphenyl)-2-(1-methyl-2-pyrrolidinyl)-ethanol and 0.5 g of triethyl amine in 20 ml methylene chloride. The mixture is stirred for 2 hours and subsequently treated with water. The organic phase is separated, dried over sodium sulphate and concentrated. There are obtained 1.5 g of the title compound as tough, light oil.

EXAMPLE 31

1-(3-methoxyphenyl)-2-(2-pyrrolidinyl)-ethanol 4.8 g of sodium borohydride are added portionwise with stirring to a solution of 6.5 g of 1-(3-methoxyphenyl)-2-(2-pyrrolidinyl)-ethanone hydrochloride in 25 ml of methanol and 5 ml of water. After 1 hour the bulk of the methanol is distilled off under a vacuum. The residue is taken up with 20 ml of water and 10 ml of 6 N sodium hydroxide solution. The mixture is extracted 5 times with, in each case, 20 ml of diethylether. The organic phases are collected, dried over sodium sulphate and concentrated to an oil which is distilled. 4.5 g of the title compound are obtained as mixture of diastereoisomers of b.p. 136° at 0.005 mm Hg.

EXAMPLE 32

10,000 tablets with an active substance content of 30 mg are produced from the following constituents:

| | |
|---|---|
| 300 g | (R*,R*)-1-(3-methoxyphenyl)-2-(1-methyl-2-pyrrolidinyl)ethanol hydrochloride (obtained according to Example 13) |
| 800 g | maize starch |
| 500 g | lactose |
| 30 g | amorphous silicic acid |
| 40 g | sodium lauryl sulfate |
| 50 g | polyvinyl pyrrolidone (average molecular weight 25,000) |
| 160 g | pectin |
| 100 g | talc |
| 20 g | magnesium stearate |
| 2000 g | |

The active substance, the maize starch, the lactose, the amorphous silicic acid and the sodium lauryl sulfate are mixed and sieved. This mixture is moistened with a solution of the polyvinylpyrrolidone in 320 ml of ethanol and granulated through a sieve with a mesh size of 1.25 mm. The granulate is dried at 40° and then mixed with pectin, talc and magnesium stearate. This mixture is compressed into tablets of 200 mg with 8 mm diameter.

EXAMPLE 33

100-liter Mixture for Ampoules

| | | |
|---|---|---|
| 1. | 1-(3-methoxyphenyl)-2-(1-methylpyrrolidin-2-yl)ethanol (obtained according to Example 11) | 2,000 g |
| 2. | mannitol | 4,000 g |
| 3. | double distilled water | to 100 liters |

1 is dissolved in about 80 liters of 3 with addition of the equivalent amount of hydrochloric acid; then 2 is added. The solution is adjusted to pH 7.0±0.5, and the volume is made up with the remainder of 3. The solution is sterilized by filtration and filled into 2 ml ampoules under sterile conditions.

EXAMPLE 34

100,000 capsules with an active substance content of 30 mg are produced from the following constitutents:

| | | |
|---|---|---|
| 1. | 3,000 g | 1-(3-methoxyphenyl)-2-(1-methyl-2-pyrrolidinyl)-ethanol (obtained according to Example 11) |
| 2. | 5,000 g | neutral oil (Miglyol ® 812) |
| | 8,000 g | |

The active substance is mixed with the neutral oil and filled into soft gelatin capsules.

EXAMPLE 35

Production of a Batch of 1,000 Suppositories 2.350 g of conventional suppository (suppocire ®BM) mass are heated to from 40° to 45°. 50 g of 1-(3-methoxyphenyl)-2-(1-methyl-2-pyrrolidinyl)ethanol (obtained according to Example 11) are stirred into the resulting melt. The obtained suppository mass is homogenized and then poured into molds.

EXAMPLE 36

Production of a 100-liter Batch of Solution 10,000 g of 1-(3-methylphenyl)-2-(1-methyl-2-pyrrolidinyl)ethanol (obtained according to Example 15) are added to 80 liters of water with vigorous stirring and addition of the equivalent amount of hydrochloric acid; subsequently, 100 g of sodium cyclamate are added, and the volume is made up to 100 liters with water. The mixture is sent through a corundum disc mill, then de-aerated and finally filled into 5 ml dropper bottles.

EXAMPLE 37

Tablets with an active substance content of 50 mg are produced from the following constituents:

| | |
|---|---|
| 1. R*,S*-1-(3-methoxyphenyl)-2-(1-methyl-2-pyrrolidinyl)ethanol (obtained according to Example 12) | 25.00 kg |
| 2. indomethacin | 25.00 kg |
| 3. cellulose (Rehocel ®) | 8.50 kg |
| 4. lactose | 25.00 kg |
| 5. maize starch | 25.00 kg |
| 6. polyvinylpyrrolidone (Kollidon ® 25) | 22.20 kg |
| 7. carboxymethylcellulose (Primojel) | 8.50 kg |
| 8. talc | 2.50 kg |
| 9. magnesium stearate | 0.30 kg |
| | 120.00 kg |

1, 2, 3, 4 and 5 are mixed, moistened with 6 (dissolved in 15 liters of water) and granulated. Thereafter, pre-drying is effected in a drying cabinet at 50°, followed by passage through a sieve. The resulting granulate is dried to a relative moisture of from 45 to 50% and, after addition of 7, 8 and 9 and careful mixing, is compressed into tablets of 120 mg weight.

Pharmacology

The distinct analgesic properties of the compounds according to the invention is evidenced on various animal species in several model experiments (hot plate test, tail flick test, writhing test) in which the said compounds, as a result of their low toxicity and absent side-effects (in particular, no occurrence of dependence or development of tolerance), prove to be superior to commercial analgesics. Neither an increase in toxicity nor a decrease in analgesic effect is detected after repeated administration. No withdrawal symptom is provoked by administration of naloxone.

A comparison of the analgesic properties of the ethanols according to the invention and of those of known strong analgesics is provided for the compounds listed in Table I.

TABLE I 1. dextropropoxyphene
2. nefopam
3. 1-(3-methoxyphenyl)-2-(1-methylpyrrolidin-2-yl)-ethanol (Example 11)
4. (R*,S*)-1-(3-methoxyphenyl)-2-(1-methyl-2-pyrrolidinyl)-ethanol (Example 12)
5. (R*,R*)-1-(3-metoxyphenyl)-2-(1-methyl-2-pyrrolidinyl)-ethanol (Example 13)
6. 2-(1-methylpyrrolidin-2-yl)-1-(3-tolyl)ethanol (Example 15)
7. (R*,S*)-1-(3-methylphenyl)-2-(1-methyl-2-pyrrolidinyl)-ethanol (Example 16)
8. (R*,R*)-1-(3-methylphenyl)-2-(1-methyl-2-pyrrolidinyl)-ethanol (Example 17)
9. 2-(1-isopropyl-2-pyrrolidinyl)-1-(3-methoxyphenyl)ethanol (Example 14).
10. 1-(3-hydroxyphenyl)-2-(1-methyl-2-pyrrolidinyl)-ethanol (Example 19)
11. 1-(3-chlorophenyl)-2-(1-methyl-2-pyrrolidinyl)-ethanol (Example 24)
12. 2-(1-n-hexyl-2-pyrrolidinyl)-1-(3-methoxyphenyl)-ethanol (Example 22)
13. (R*,S*)-acetic acid-[1-(3-methoxyphenyl)-2-(1-methyl-2-pyrrolidinyl)-ethyl]-ester (Example 28)

Table II presents the $LD_{50}$ and $ED_{50}$ values [mg/kg] obtained after oral application in various analgesia tests.

TABLE II

Comparison of Toxicity $LD_{50}$[mg/kg, per os] and Analgesic Effect [$ED_{50}$ values (mg/kg, per os)] of Known Analgesics and of Subst. 1-phenyl-2-pyrrolidin-2-yl-ethanols

| Compound Serial No. according to Table I | $LD_{50}$ Mouse | $ED_{50}$ | | | |
|---|---|---|---|---|---|
| | | Hot plate | Mouse Tail-Flick | Writhing | Rat Tail-Flick |
| 1 | 140 | 15 | 25 | 30 | 25 |
| 2 | 180 | 30 | 20 | 25 | 10 |
| 3 | 600 | 30 | 25 | 15 | 7 |
| 4 | 420 | 100 | 60 | 50 | — |
| 5 | 490 | 50 | 70 | 40 | — |
| 6 | 420 | 100 | 35 | 75 | 10 |
| 7 | 300 | 100 | 50 | 75* | — |
| 8 | 320 | 100* | 10 | 75* | — |
| 9 | 340 | 100* | 75* | 75 | |
| 10 | 420 | — | — | 125 | — |
| 11 | 330 | — | 65 | 125 | — |
| 12 | 180 | — | 70 | 75* | — |
| 13 | 440 | — | — | 75* | — |

*$ED_{40}$-values

According to Way et al. [*J. Pharmacol. Exp. Ther.*, 167 (1969) 1] mice, which are dependent on analgesics with a morphine-like effect, react with withdrawal jumping immediately after intraperitoneal administration of naloxone. According to Saelens and co-workers [*Arch. Int. Pharmacodyn. Ther.*, 190 (1971) 213] for 1, too, a dependence development is evidenced. 2 cannot be tested accordingly because of its toxicity.

3 and 6 were administered to mice [200 mg/kg twice daily over 5 weekdays]. The intraperitoneal application of 30 mg/kg of naloxone 1 hour after administration of the last dose of the compounds according to the invention did not lead to withdrawal jumping in the animals treated with the compounds according to the invention (cf. Table III).

Table III

Withdrawal jumping of mice after treatment with several compounds and intraperitoneal application of naloxone

| treatment with | % of the animals reacting with "jumping" |
|---|---|
| NaCl; 0.9% aqueous solution | 20 |
| 1 | 100 |
| 2 | not testable; lethality 80% |
| 3 | 20 |
| 6 | 10 |

Tests with the substituted 1-phenyl-2-pyrrolidin-2-yl-ethanols on the mouse and on the rat in the sub-toxic dosage range (reserpin antagonism, haloperidol antagonism, hexobarbital narcosis, perphenazine and tetrabenazine antagonism) yield no indication of specific side-effects.

The determination of pharmacological properties was effected according to the following methods:

Analgesia (a) Hot plate test: female albino mice were placed on a 50° C. hot plate and the reaction time until they licked their paws was recorded with a stop watch. Normal values lie in the range of from 7 to 8 seconds. The substances tested cause delayed reaction to the heat stimulus, i.e. reduced thermal-pain sensitivity. The dose which prolongs the reaction time by 50% was determined. Literature: Eddy, N. B., and Leimbach, D., *J. Pharmacol. Exp. Ther.*, 107 (1953) 385.

(b) Tail-Flick test: a thermal pain is caused at the tail root of female albino mice or rats with a focused heat ray, and the time until the tail is drawn away is recorded with a stop watch. Normally, it lies in the range of from 4 to 5 seconds. The substances tested cause delayed reaction to the heat pain, i.e. reduced thermal-pain reaction. The dose which prolongs the reaction time by 50% was determined. Literature: D'Amour, F. E., and Smith, D. L., *J. Pharmacol. Exp. Ther.*, 72 (1941) 74.

(c) Writhing test (acetic acid writhing): intraperitoneal injection of 0.2 ml/20 g mouse of a 0.75% strength acetic acid solution induces (in albino mice) a typical syndrome, called writhing, which proceeds over the body with dorsal flection. These writhings, which occur in the course of the first half hour after administration, are counted in the space of time of from 5 to 20 minutes after administration. The substances tested cause a reduction of the number of writhing syndromes. The dose which reduces the number of writhings by 50%, with reference to the daily control, was determined. Literature: Koster, Anderson, *Fed. Proc.*, 18 (1959) 42.

Determination of the Lethal Effect

The toxicity investigations were carried out on female NMRI mice: body weight 22 to 26 g. The animals received food and water (Altromin ®) *ad libitum*. The substances to be tested were administered orally with the oesophageal sound as solutions of various concentration in a volume of from 10 to 20 ml/kg; 5 animals per dose were kept in Makrolon ® cages, Type II. The observation duration was 48 hours. The $DL_{50}$, the dose with which 50% of the animals died, was determined graphically from the dose effect curve.

The preceding disclosure adequately apprises those of ordinary skill in the relevant art:

a. what the subject invention is, including its metes and bounds;

b. how to make and use the novel compounds from known chemicals or from chemicals which are synthesized by established and recognized procedures from available starting materials;

c. how to prepare the novel compositions; and d. how to use the compounds and the compositions, and makes it clear that changes in structure and composition components are readily made without departing from the spirit or scope of the instant teachings.

What is claimed is:

1. A compound which, in free-base form, is of the formula

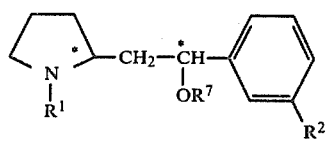

wherein
  $R^1$ is $-C_{n-1}H_{2n-1}$;
  $R^2$ is chloro, hydroxy, alkyl with from 1 to 4 carbon atoms or alkoxy with from 1 to 4 carbon atoms;
  $R^7$ is a hydrogen atom, carboxylic acid acyl, alkyl with from 1 to 7 carbon atoms or tetrahydropyranyl;
  n is a positive whole number of at most 8 and
  * designates an asymmetric carbon atom.

2. A compound according to claim 1 wherein $R^7$ is alkyl with from 1 to 3 carbon atoms or tetrahydropyranyl.

3. A compound according to claim 1 wherein $R^7$ is alkanoyl with from 2 to 7 carbon atoms.

4. A compound according to claim 1 wherein $R^7$ is hydrogen.

5. A compound according to claim 1 in the form of the free base.

6. A compound according to claim 1 in the form of an acid-addition salt.

7. A pharmacologically-acceptable compound according to claim 6.

8. A compound according to claim 4 wherein $R^1$ is -H.

9. A compound according to claim 4 wherein $R^1$ is alkyl.

10. A substituted 1-phenyl-2-pyrrolidinyl-2-ylethanol according to claim 4 wherein
  $R^1$ is -H or alkyl with from 1 to 3 carbon atoms and
  $R^2$ is -OH, methyl or methoxy,
or an acid-addition salt thereof.

11. A pharmacologically-acceptable compound according to claim 10 wherein $R^1$ is -H or methyl and $R^2$ is methyl or methoxy.

12. A compound according to claim 10 which is 1-(3-methoxyphenyl)-2-pyrrolidin-2-yl-ethanol or an acid-addition salt thereof.

13. A compound according to claim 10 which is 2-(1-methylpyrrolidin-2-yl)-1-(m-tolyl)ethanol or an acid-addition salt thereof.

14. A compound according to claim 10 which is 1-(3-methoxyphenyl)-2-(1-methylpyrrolidin-2-yl)-ethanol or an acid-addition salt thereof.

15. A compound according to claim 1 which is a diastereoisomer, an enantiomer, a racemate or any combination thereof.

16. A pharmaceutical composition containing active principle and inert material and wherein the active principle comprises an analgesically-effective amount of a pharmacologically-acceptable compound of claim 1 when the composition is in unit-dosage form.

17. A process for preventing or alleviating pain which comprises administering to a mammal subject to or afflicted with pain an analgesically-effective amount of one or a combination of pharmacologically-acceptable compounds according to claim 1.

18. A pharmacologically-acceptable compound according to claim 1 wherein acyl is alkanoyl with up to 11 carbon atoms.

19. A pharmacologically-acceptable compound according to claim 18 wherein $R^2$ is chloro.

20. A pharmacologically-acceptable compound according to claim 18 wherein $R^2$ is hydroxy.

21. A pharmacologically-acceptable compound according to claim 18 wherein $R^2$ is alkyl with from 1 to 4 carbon atoms.

22. A pharmacologically-acceptable compound according to claim 18 wherein $R^2$ is alkoxy with from 1 to 4 carbon atoms.

* * * * *

UNITED STATES PATENT AND TRADEMARK OFFICE
CERTIFICATE OF CORRECTION

PATENT NO. : 4,198,424
DATED : April 15, 1980
INVENTOR(S) : Klaus Eistetter and Hans-Peter Kley It is certified that error appears in the above-identified patent and that said Letters Patent are hereby corrected as shown below:

Cover page, in [30] Foreign Application Priority Data, "Dec. 1, 1977" should read --Dec. 2, 1977--. Column 2, approximately line 7 [in the pyrrolidine entity of formula (I)], the asterisk should designate the 2-position

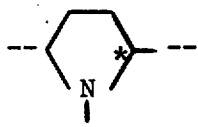

of the ring; line 30, "alkoxy group" should read --alkoxy groups--. Column 3, line 64, "(addition)" should read --(addiction)--. Column 6, line 42, "1-phenyl-2- 2-yl-ethanols" should read --1-phenyl-2-pyrrolidin-2-yl-ethanols--; line 55 [in the pyrrolidine entity of formula (II)], the asterisk should designate the 2-position

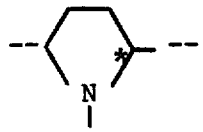

Column 17, line 65, "metoxyphenyl" should read --methoxyphenyl--. Column 20, line 37, "1-phenyl-2-pyrrolidinyl-2-ylethanol" should read --1-phenyl-2-pyrrolidinyl-2-yl-ethanol; line 51, "(m-tolyl)" should read --(*m*-tolyl)--.

Signed and Sealed this

Fourth Day of November 1980

[SEAL]

Attest:

SIDNEY A. DIAMOND

Attesting Officer

Commissioner of Patents and Trademarks